(12) United States Patent
Hashimshony et al.

(10) Patent No.: US 9,999,353 B2
(45) Date of Patent: *Jun. 19, 2018

(54) MEDICAL DEVICE AND METHOD FOR USE IN TISSUE CHARACTERIZATION AND TREATMENT

(71) Applicant: DUNE MEDICAL DEVICES LTD., Caesarea (IL)

(72) Inventors: Dan Hashimshony, Pardes Hana (IL); Gil Cohen, Jerusalem (IL); Gal Aharonowitz, Moshav Gan Haim (IL)

(73) Assignee: DUNE MEDICAL DEVICES LTD., Caesarea (IL)

(*) Notice: Subject to any disclaimer, the term of this patent is extended or adjusted under 35 U.S.C. 154(b) by 591 days.

This patent is subject to a terminal disclaimer.

(21) Appl. No.: 13/856,340

(22) Filed: Apr. 3, 2013

(65) Prior Publication Data

US 2013/0267821 A1 Oct. 10, 2013

Related U.S. Application Data

(63) Continuation-in-part of application No. 13/547,950, filed on Jul. 12, 2012, now Pat. No. 9,757,098, which
(Continued)

(51) Int. Cl.
*A61B 17/00* (2006.01)
*A61B 5/00* (2006.01)
(Continued)

(52) U.S. Cl.
CPC ........ *A61B 5/0059* (2013.01); *A61B 10/0275* (2013.01); *A61B 17/3205* (2013.01);
(Continued)

(58) Field of Classification Search
CPC ............ A61B 17/32056; A61B 5/0059; A61B 10/0275; A61B 17/3205;
(Continued)

(56) References Cited

U.S. PATENT DOCUMENTS 3,910,279 A 10/1975 Okada et al.
5,630,426 A 5/1997 Eggers et al.
(Continued)

FOREIGN PATENT DOCUMENTS

JP 2003520062 A 7/2003
JP 2008165680 A 7/2008
(Continued)

OTHER PUBLICATIONS

Jan. 24, 2013 Search Report issued in EP Application No. 12168882.4.

*Primary Examiner* — Sean Dougherty
(74) *Attorney, Agent, or Firm* — Browdy and Neimark, PLLC

(57) ABSTRACT

A medical device is presented for use in tissue characterization and treatment. The device comprises a tissue characterization probe comprising an elongated carrier carrying an array of tissue characterization sensors which are arranged in a spaced-apart relationship on at least a part of the carrier with known distances between them along a longitudinal axis of the carrier and along at least part of a circumference of the carrier, such that during progression of the probe through a tissue mass each of the sensors generates tissue characterization signals from successive locations thereof within the tissue mass enabling to locate an abnormal tissue inside said tissue mass, thereby enabling consequent treatment of the abnormal tissue. Several movement mechanisms are described for enabling relative movement between the carrier and a treatment tool passing therethrough.

33 Claims, 12 Drawing Sheets
(7 of 12 Drawing Sheet(s) Filed in Color)

Related U.S. Application Data is a continuation-in-part of application No. 12/663,923, filed as application No. PCT/IL2008/000965 on Jul. 13, 2008, now Pat. No. 9,301,734.

(60) Provisional application No. 60/950,081, filed on Jul. 16, 2007.

(51) Int. Cl.
*A61B 10/02* (2006.01)
*A61B 17/3205* (2006.01)

(52) U.S. Cl.
CPC .......... *A61B 17/32056* (2013.01); *A61B 2017/00026* (2013.01); *A61B 2017/00039* (2013.01); *A61B 2017/00057* (2013.01)

(58) Field of Classification Search
CPC .......... A61B 2017/00057; A61B 2017/00026; A61B 2017/00039
See application file for complete search history.

(56) References Cited

U.S. PATENT DOCUMENTS

| | | | |
|---|---|---|---|
| 5,800,350 A | 9/1998 | Coppleson et al. | |
| 5,830,146 A * | 11/1998 | Skladnev | A61B 5/0084 600/121 |
| 5,846,513 A | 12/1998 | Carroll et al. | |
| 5,989,199 A * | 11/1999 | Cundari | A61B 5/0053 600/587 |
| 6,006,755 A | 12/1999 | Edwards | |
| 6,022,362 A | 2/2000 | Lee et al. | |
| 6,120,437 A | 9/2000 | Yoon et al. | |
| 6,321,109 B2 | 11/2001 | Ben-Haim et al. | |
| 6,331,166 B1 | 12/2001 | Burbank et al. | |
| 6,419,635 B1 | 7/2002 | Hedengren et al. | |
| 6,419,640 B1 | 7/2002 | Taylor | |
| 6,440,147 B1 * | 8/2002 | Lee et al. | 606/159 |
| 6,689,145 B2 | 2/2004 | Lee et al. | |
| 6,780,179 B2 | 8/2004 | Lee et al. | |
| 6,813,515 B2 | 11/2004 | Hashimshony | |
| 7,101,378 B2 | 9/2006 | Salameh et al. | |
| 7,122,011 B2 | 10/2006 | Clifford et al. | |
| 7,184,824 B2 | 2/2007 | Hashimshony | |
| 8,413,582 B1 * | 4/2013 | Chen | 102/232 |
| 9,757,098 B2 * | 9/2017 | Hashimshony | A61B 10/0275 |
| 2001/0047169 A1 | 11/2001 | McGuckin, Jr. et al. | |
| 2001/0056236 A1 | 12/2001 | Angelsen | |
| 2002/0019597 A1 | 2/2002 | Dubrul et al. | |
| 2002/0026127 A1 * | 2/2002 | Balbierz | A61B 18/1206 600/567 |
| 2002/0035361 A1 | 3/2002 | Houser et al. | |
| 2002/0103417 A1 * | 8/2002 | Gazdzinski | A61B 1/00016 600/109 |
| 2002/0128643 A1 * | 9/2002 | Simpson | A61B 18/1492 606/34 |
| 2003/0009110 A1 * | 1/2003 | Tu et al. | 600/547 |
| 2003/0050574 A1 | 3/2003 | Krueger | |
| 2003/0055423 A1 | 3/2003 | Levinson | |
| 2003/0138378 A1 | 7/2003 | Hashimshony | |
| 2004/0243018 A1 * | 12/2004 | Organ | A61B 5/053 600/547 |
| 2004/0255739 A1 | 12/2004 | Clifford et al. | |
| 2004/0267165 A1 * | 12/2004 | Sarvazyan | A61B 5/0002 600/587 |
| 2005/0033199 A1 * | 2/2005 | van der Steen | A61B 8/12 600/587 |
| 2005/0203419 A1 | 9/2005 | Ramanujam et al. | |
| 2006/0041199 A1 * | 2/2006 | Elmaleh | A61B 5/0071 600/478 |
| 2006/0235286 A1 * | 10/2006 | Stone | A61B 5/02007 600/381 |
| 2006/0253107 A1 * | 11/2006 | Hashimshony | A61B 5/0084 606/1 |
| 2006/0259026 A1 * | 11/2006 | Godara | A61B 18/1482 606/41 |
| 2006/0270942 A1 * | 11/2006 | McAdams | A61B 5/0531 600/547 |
| 2007/0118027 A1 * | 5/2007 | Baker, Jr. | A61B 5/0059 600/310 |
| 2008/0039742 A1 * | 2/2008 | Hashimshony | A61B 5/0071 600/587 |
| 2008/0214955 A1 | 9/2008 | Speeg et al. | |
| 2008/0221484 A1 * | 9/2008 | Sarvazyan | A61B 5/103 600/587 |
| 2008/0287750 A1 * | 11/2008 | Hashimshony | A61B 5/00 600/301 |
| 2009/0005707 A1 * | 1/2009 | Sarvazyan | A61B 5/1077 600/587 |
| 2010/0168611 A1 | 7/2010 | Hashimshony et al. | |
| 2010/0222647 A1 * | 9/2010 | Hashimshony | A61B 1/04 600/301 |
| 2011/0034806 A1 * | 2/2011 | Hartov | A61B 5/0536 600/443 |
| 2012/0316463 A1 | 12/2012 | Hashimshony et al. | |
| 2012/0323134 A1 * | 12/2012 | Cory | A61B 5/4893 600/547 |
| 2013/0072815 A1 | 3/2013 | Hashimshony et al. | |
| 2013/0177972 A1 * | 7/2013 | Green et al. | 435/288.7 |
| 2013/0267821 A1 * | 10/2013 | Hashimshony | A61B 17/32056 600/407 |

FOREIGN PATENT DOCUMENTS

| | | |
|---|---|---|
| JP | 2009136377 A | 6/2009 |
| JP | 2009526554 A | 7/2009 |
| JP | 2010512848 A | 4/2010 |
| WO | WO 92/17108 A1 | 10/1992 |
| WO | WO 98/12968 | 4/1998 |
| WO | WO 99/44506 A1 | 9/1999 |
| WO | 00/69335 A1 | 11/2000 |
| WO | WO 01/74252 A2 | 10/2001 |
| WO | WO 01/82998 A2 | 11/2001 |
| WO | WO 2006/103665 A2 | 10/2006 |
| WO | WO 2007/015255 A2 | 2/2007 |
| WO | WO 2007/083310 A2 | 7/2007 |
| WO | 2007/149595 A2 | 12/2007 |
| WO | 2008/076712 A2 | 6/2008 |
| WO | WO 2009/010960 A2 | 1/2009 |
| WO | WO 2011/016035 A1 | 2/2011 |
| WO | 2012/092016 A1 | 7/2012 |

\* cited by examiner

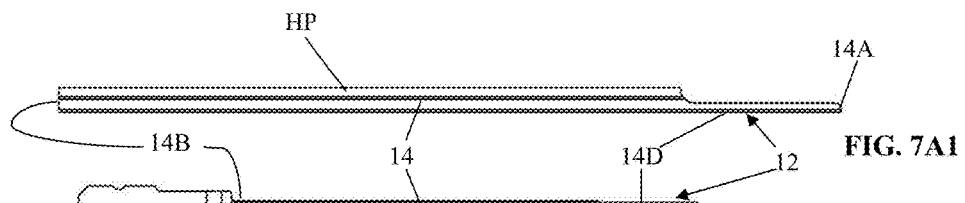
FIG. 7A1
FIG. 7A2
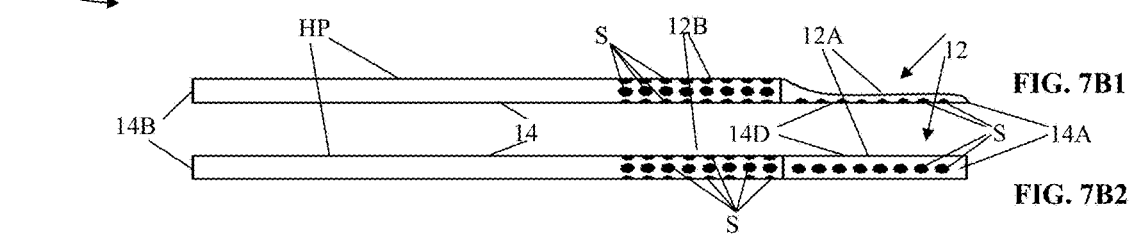
FIG. 7B1
FIG. 7B2
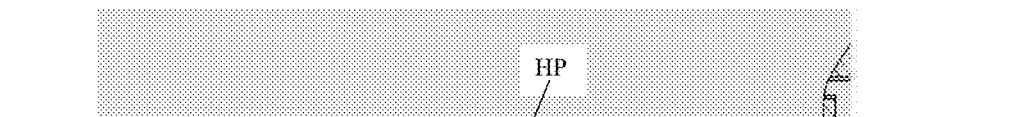
FIG. 7C
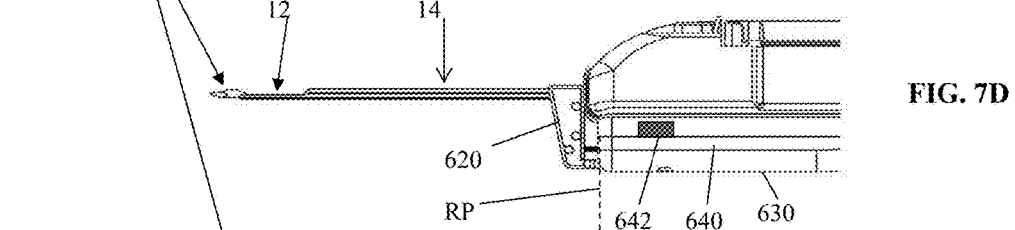
FIG. 7D
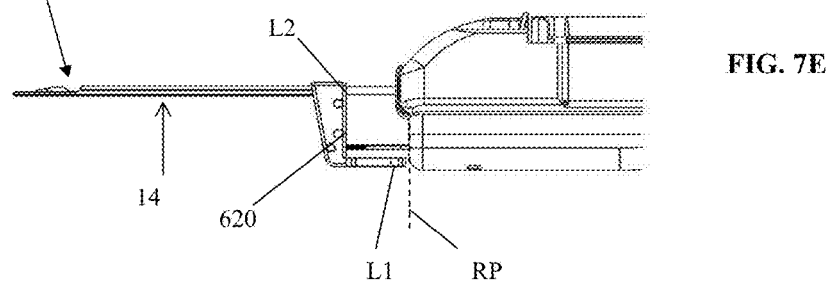
FIG. 7E

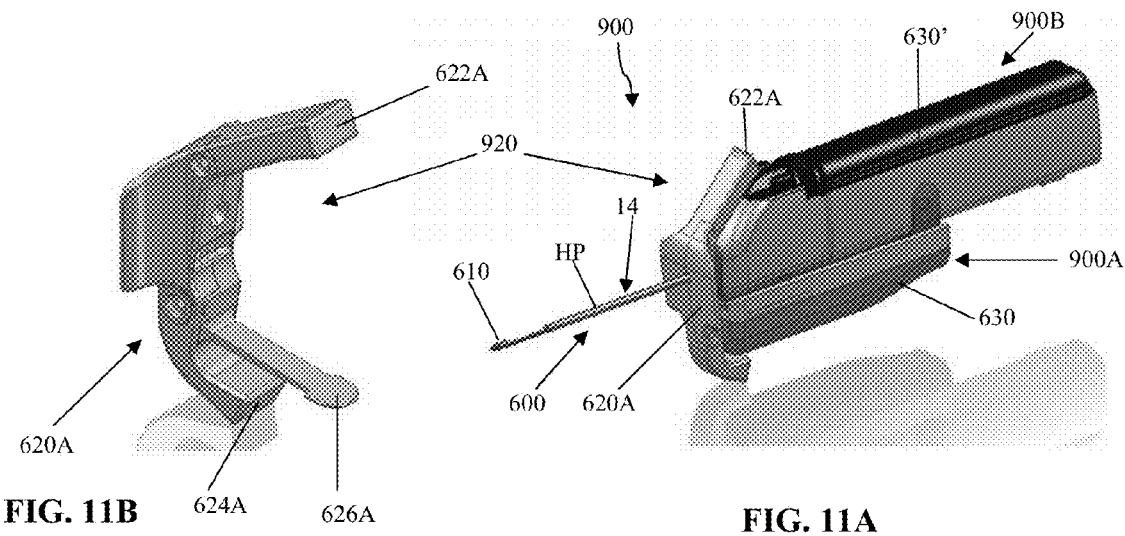
FIG. 11B   FIG. 11A
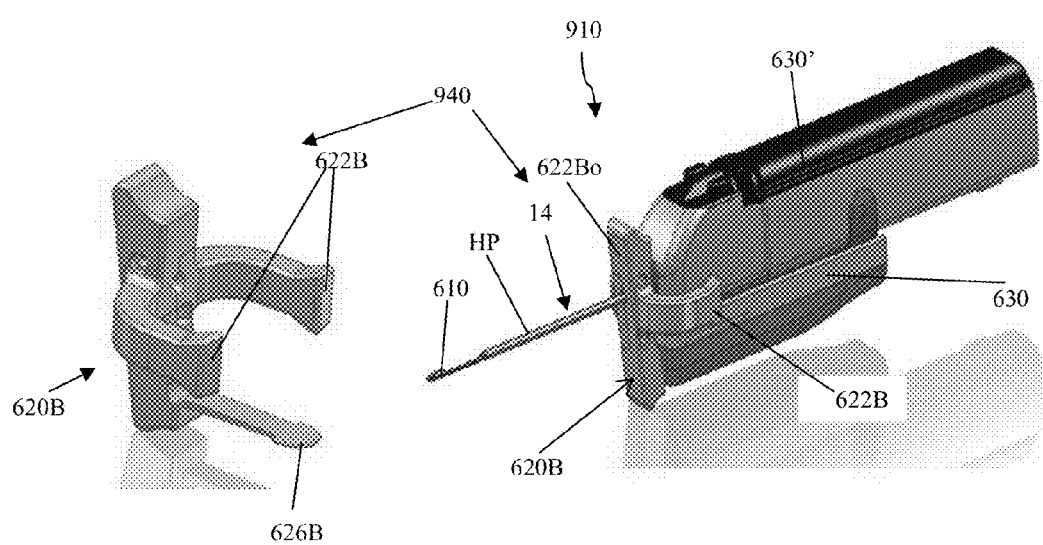
FIG. 12B   FIG. 12A

MEDICAL DEVICE AND METHOD FOR USE IN TISSUE CHARACTERIZATION AND TREATMENT

This is a Continuation-in-Part of U.S. patent application Ser. No. 13/547,950 filed Jul. 12, 2012, which in turn is a Continuation-in-Part of U.S. patent application Ser. No. 12/663,923 filed Dec. 10, 2009, which is a U.S. National Stage of International Patent Application No. PCT/IL08/00965 filed Jul. 13, 2008, which claims the benefit of U.S. Provisional Patent Application No. 60/950,081 filed Jul. 16, 2007. The disclosure of each of the prior applications is hereby incorporated herein by reference in its entirety.

FIELD OF THE INVENTION

This invention relates to medical devices and methods for use in tissue characterization and treatment.

BACKGROUND

Techniques for identifying abnormal (e.g. tumorous) cells in a biological tissue are generally known. Such techniques include those utilizing determination of the electrical properties of a tissue, for example, by determination of electrical impedance or dielectric constants. Some kinds of tumors can be identified by determining differences in the measured electrical properties of the tissue. The identified and located region of abnormal tissue can then be treated and/or removed from the body Various types of tissue characterization sensor and its integration with a tissue treatment/removal tool are described in the following patent publications, all assigned to the assignee of the present application: US2003138378, WO2006103665, WO02007015255, U.S. Pat. No. 6,813,515 and U.S. Pat. No. 7,184,824.

Also, various techniques are known for removing a certain tissue specimen from a tissue mass. These techniques are disclosed for example in U.S. Pat. No. 6,689,145 and U.S. Pat. No. 7,122,011.

GENERAL DESCRIPTION

There is a need in the art to facilitate precise location and determination of a volume of a tissue specimen (e.g. abnormal tissues) to be treated (e.g. removed). Also, there is need in the art for a tissue treatment technique capable of adjusting a treatment volume to the determined volume of the abnormal tissue specimen.

The present invention solves the above problems by providing a novel medical device for use in tissue characterization and treatment. The device comprises a tissue characterization probe comprising an elongated carrier carrying an array of tissue characterization sensors which are located at least within a distal portion of the carrier and are arranged in a spaced-apart relationship with known distances between them along a longitudinal axis of said carrier and along at least a part of circumference of the carrier, such that during progression of the probe through a tissue mass each of the sensors generates tissue characterization signals from successive locations thereof within the tissue mass enabling to locate an abnormal tissue inside said tissue mass thereby enabling consequent treatment of the abnormal tissue.

In one embodiment, the array of tissue characterization sensors covers the whole circumference at least at part of said distal portion of the carrier.

According to some embodiments, the elongated carrier has two integral portions including said distal portion and a hollow portion extending between a proximal end of the carrier and the distal portion. The carrier is configured for passing a treatment tool through the hollow portion thereof and enables at least a part of the treatment tool to project from the hollow portion and extend along the distal portion.

The device of the invention may comprise a treatment tool carried by said elongated carrier.

The treatment tool may be configured for carrying out at least one of the following: biopsy, cutting, delivering physical treatment, delivering treatment medication, diagnostics. In some embodiments of the invention, the treatment tool is carried by (e.g. mounted on or inside) the characterization probe carrier. In some embodiments, the treatment tool may be selectively shiftable between its inoperative position being located substantially entirely inside the carrier and its operative position projecting by at least one tissue treating portion towards outside the carrier. The dimension of the tissue treating portion(s) projectable from the carrier, and possibly also location of the tissue treating portion(s) with respect to the carrier can be controllably varied.

In some embodiments of the invention, the probe carrier is formed with a guiding cutting tool, to facilitate insertion of the probe towards a targeted location in the tissue. Also, in some embodiments of the invention, a marker may be left in the body, at the location of the tissue being treated (removed).

In some embodiments of the invention, the treatment tool may be carried by the characterization probe. The configuration may be such that the treatment tool is an integral part of the medical device, or is removably mountable thereon (e.g., on the tissue characterization probe), for example allowing for subsequent changing between different kinds of treatment tools (such as cutting, biopsy, delivering physical treatment, delivering treatment medication, diagnostics), with relative ease and speed. The technique of the invention, enabling determination of the dimension of the abnormal tissue specimen, as well as consequent or immediate treatment of said specimen allows for precise, effective treatment even for very small and local tissue mass. Moreover, the technique may be even more precise when the treatment tool may be activated at the immediate vicinity of the sensors or at the exact location of an individual sensor, without moving the sensors from place.

In some embodiments, the distal portion is configured as a trough like member thereby enabling concurrent alignment of a distal portion of the treatment tool at one side of the distal portion and the array of tissue characterization sensors at opposite side of the distal portion to the same segment of the tissue mass.

The device may comprise a handle portion connectable to or integral with the proximal end of the carrier. The handle may be configured for engaging with a handle portion of the treatment tool when the treatment tool is inserted into the hollow portion of the carrier.

According to some embodiments of the invention, the device comprises a movement mechanism located at the proximal end of the carrier, and being configured and operable to enable relative displacement between the carrier and the treatment tool.

The movement mechanism may be located inside the handle, and the device is configured and operable to enable relative displacement between the carrier and the treatment tool.

The movement mechanism may comprise a registration assembly to define a reference position for the array of tissue characterization sensors with respect to a certain reference plane defined by the device, thereby enabling to monitor repositioning of the tissue characterization sensors caused by movement of the carrier with respect to the reference plane. The registration assembly may comprise a sensing unit configured and operable to identify a position of the sensors array relatively to said reference plane and to generate data indicative thereof.

According to another embodiment, the movement mechanism is located at the proximal end of the carrier, and being configured and operable to enable relative displacement between the carrier and the treatment tool. The movement mechanism comprises a registration assembly to define a reference position for the array of tissue characterization sensors with respect to a certain reference plane defined by the handle.

The registration assembly may comprise an L-like shaped bracket which by its one arm of a given length is movably connected to the handle and by its other arm is connected to the carrier. The reference plane is defined by a distal edge of the handle, thereby enabling to monitor repositioning of the tissue characterization sensors caused by movement of the bracket with respect to the reference plane.

There are several options for configuring the movement mechanism. For example, the movement mechanism may comprise a locking system configured to maintain the sensor array at fixed and locked positions.

Further, the movement mechanism may comprise a slider configured to selectively displace the treatment tool between inoperative and operative positions.

The movement mechanism may be configured to convert a rotational movement into the linear relative displacement between the carrier and the treatment tool.

The movement mechanism may comprise rack and pinion configuration.

According to some embodiments of the invention, the device may be configured as a two-part assembly comprising a first assembly and a second assembly, the first and second assemblies being removably attachable to one another.

The first assembly may carry the tissue characterization probe and the second assembly carries the treatment tool.

Alternatively, both of the tissue characterization probe and the treatment tool may be carried by either the first assembly or the second assembly.

Preferably, the device comprises a control unit configured for receiving and analyzing tissue characterizing signals from each of all the sensors and utilizing data indicative of the respective sensors' location for determining a dimension of an abnormal tissue specimen, thereby enabling consequent treatment of the abnormal tissue specimen by the treatment tool. The control unit may comprise a graphical user interface configured for presenting information related to the signals received from all the sensors, thereby providing an operator with information regarding the tissue type at the locations of the sensors, and facilitating analysis of the location and extent of the tissue to be treated.

According to one more broad aspect of the invention, the device may comprise an array of tissue characterization sensors being coupled to a flexible signal transmission structure by at least one common continuous surface.

Yet according to another broad aspect of the invention, there is provided a medical device for use in tissue characterization and treatment, the device comprises a tissue characterization probe comprising an elongated carrier having a hollow portion for passing therein a treatment tool, an array of tissue characterization sensors which are located on the carrier at least within a distal portion thereof and are arranged in a spaced-apart relationship with known distances between them enabling to locate an abnormal tissue inside a tissue mass during progression of the probe through the tissue mass based on tissue characterization signals from the array of sensors and to perform consequent treatment of a tissue specimen by the treatment tool; and a movement mechanism located at the proximal end of the carrier, and being configured to enable relative displacement between the carrier and the treatment tool. As described above, in some embodiments, the distal portion is configured as a trough like member enabling concurrent alignment of the distal portion of the treatment tool and the array of tissue characterization sensors with the same segment of the tissue mass. As also mentioned above, the treatment tool may be selectively shiftable between its inoperative position being located substantially entirely inside the hollow portion of the carrier and its operative position projecting by its at least one tissue treating portion towards the distal portion of the carrier.

According to some embodiments, the treatment tool and the carrier are configured to enable the treatment tool to be selectively shiftable between its inoperative position being located substantially entirely inside the hollow portion of the carrier and its operative position projecting by its at least one tissue treating portion towards outside the carrier when a part of the treatment tool extends along the distal portion of the carrier.

BRIEF DESCRIPTION OF THE DRAWINGS

The patent or application file contains at least one drawing executed in color. Copies of this patent or patent application publication with color drawings will be provided by the Office upon request and payment of the necessary fee.

In order to understand the invention and to see how it may be carried out in practice, embodiments will now be described, by way of non-limiting example only, with reference to the accompanying drawings, in which:

FIGS. 7A1-7A2 and 7B1-7B2 show two examples, respectively, of the device configuration utilizing probes configured generally as shown in FIGS. 1A and 1B, where a treatment tool can be applied to the desired location, identified by the tissue characterization sensors, while allowing the sensors to be kept in place;

FIGS. 7C-7E exemplify more specifically attachment of the probe with the treatment tool to a hand held device;

FIG. 11A illustrates an example of a tissue treatment apparatus and a manual movement mechanism having another bracket configuration utilizing the medical device of the present invention;

FIG. 11B is an enlarged side view of a possible configuration of the bracket element;

FIG. 12A illustrates an example of a tissue treatment apparatus and a manual movement mechanism having another bracket configuration utilizing the medical device of the present invention;

FIG. 12B is an enlarged side view of another possible configuration of the bracket element;

DETAILED DESCRIPTION OF EMBODIMENTS

Figure 1A:
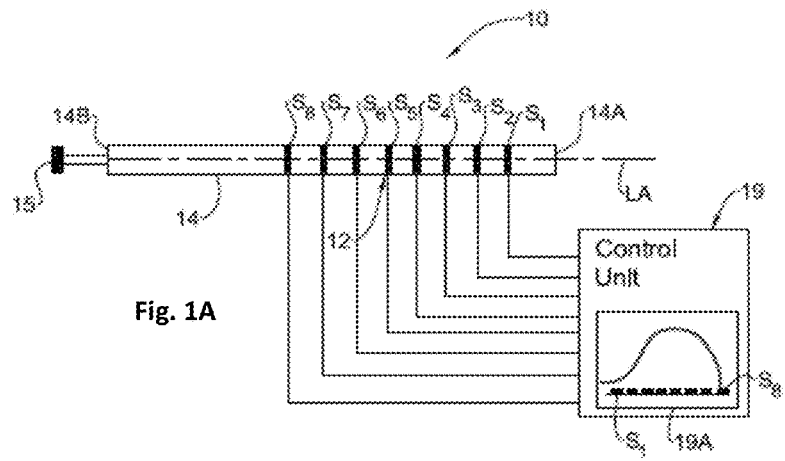
FIGS. 1A and 1B are schematic illustrations of examples of a medical device of the present invention.
Figure 1B:
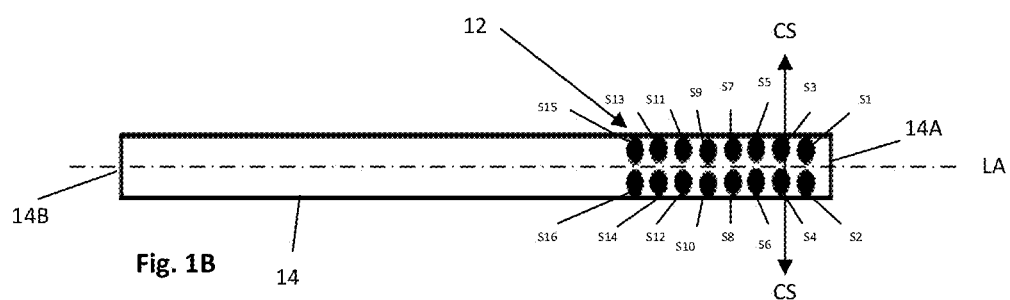

Referring to FIGS. 1A and 1B, there is schematically illustrated a medical device, generally designated 10, according to some embodiments of the invention. The device 10 is configured for use in tissue characterization and treatment, and includes a tissue characterization probe 12 carried by an elongated shaft/carrier 14, which has distal and proximal ends 14A and 14B, respectively, and is formed with a control handle 15 at its proximal end 14B. The tissue characterization probe 12 includes a plurality of tissue characterization sensors.

The tissue characterization sensor array may include one or more of optical, radiofrequency (RF), microwave (MW), electrical, magnetic, temperature, elastic, biological, chemical, radioactive-emission, and mechanical sensors of any known type. The construction and operation of the tissue characterization sensor does not form part of the present invention, and therefore need not be specifically described. For example, sensors described in the above indicated patent publications assigned to the assignee of the present application may be used.

Figure 1C:
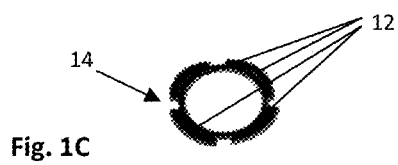
FIG. 1C shows a cross sectional view of a probe of FIG. 1B.

The plurality of sensors may be arranged in a one-dimensional array where the sensors are arranged on the surface of the carrier 14 in a spaced-apart relationship only along the longitudinal axis thereof, or may be arranged in a two-dimensional array being in a spaced apart relationship along the longitudinal and lateral axes of the carrier (as may be constituted by example of FIG. 1B). In case of a rounded probe (substantially circular cross section), the sensors may be arranged in a two-dimensional array being in a spaced-apart relationship along the carrier's axis LA and also along at least a part of the circumference of the carrier, as seen in FIGS. 1B and 1C. At times, the two-dimensional array of the tissue characterization sensors is actually a flexible structure that wraps at least a part of the probe. Such a flexible structure may be implemented as described in WO 2011/016035 which is assigned to the assignee of this application and is incorporated herein by reference with respect to this specific and not limiting example.

In the example of FIG. 1A, a plurality of eight sensors $S_1$-$S_8$ is shown, the sensors $S_1$-$S_8$ are arranged in a spaced-apart relationship along a longitudinal axis LA of the carrier 14, and may be arranged in one- or two dimensional array. For example, the sensor array may include, in addition to a group of sensors arranged in one-dimensional array, sensors arranged in a spaced-apart manner along a circumferential region of the carrier. The sensor array gives, in real time, indication about the nature of tissue along the carrier 14.

FIG. 1B exemplifies more specifically another possible configuration of the medical device 10 in which a two-dimensional array of sensors is provided on the carrier 14 extending both along the carrier's axis and its circumference. There are 16 sensors being seen in the figure, but it should be clear that there might be more sensors in the array, for example sensors that cannot be seen in this side view of the probe.

FIG. 1C shows the cross sectional view of a carrier 14 taken along the line CS-CS in FIG. 1B. As shown in this example, the sensors are arranged in a spaced-apart relationship along the entire circumference of the carrier. This configuration allows monitoring the surrounding tissue in all directions without the need for turning the probe.

The sensors are spaced from one another a known distance, which may or may not be equal for all the sensors in the array. The known relative locations of the sensors along the carrier's 14 axis and possibly also along the circumference (or lateral axis in general) allows for identifying corresponding locations in a tissue mass when the probe is progressing through the tissue mass (i.e. scans the tissue) based on signals received from the sensors. In this connection, the medical device 10 is associated with an appropriate control system 19 configured for receiving and analyzing the signals generated by the sensors. It should be understood that connection between the sensors and the control unit is shown in the figure schematically, and in case a wired connection is used between the sensors and the control unit, the wires would extend inside the carrier 14 and exit at the proximal end 14B. The sensors may be connected to the control system using a flexible signal transmission structure as disclosed in the above mentioned WO 2011/016035 assigned to the assignee of the present application.

The control system may be an external system connectable (via wires or wireless signal transmission) to the sensors, or may be a constructional part of the probe itself. The control system, based on the analysis of the received signals, operates for determining a location of the margins of an abnormal tissue region inside the examined tissue mass and generating output data indicative of a dimension of the abnormal tissue region. This allows for consequent treatment of the abnormal tissue region by an appropriate treatment tool.

The control system preferably includes a graphical user interface (GUI) 19A, and is configured for presenting information related to the signals received from each of the sensors. The signals received from each sensor are indicative of the relative position of that sensor and the tissue property(ies) at said location. The GUI thus presents a map of the tissue property(ies) along the probe propagation axis and preferably also around the probe (i.e. angular resolution at a given location on the probe), obtained without a need to rotate the probe. This information provides the operator with information regarding the tissue type at the locations of the sensors. The information presented on the GUI may assist the operator in analyzing the location and extent of the tissue to be treated. The GUI may be configured as described in co-pending U.S. application Ser. No. 13/676,993, which is incorporated herein by reference.

Generally, the treatment tool may be configured for carrying out one or more of the following: biopsy, cutting, delivering physical treatment, delivering treatment medication, diagnostics. More specifically, the present invention is used for removal of an intact tissue specimen (abnormal tissue) and is therefore described below with respect to this specific but not limiting example.

Preferably, the probe 12 also carries a treatment tool, e.g. a cutting tool. This is implemented by configuring the probe such that the treatment tool can be selectively shiftable between its inoperative position, when it is located substantially entirely inside the carrier 14, and its operative positions when its one or more excision elements (constituting one or more tissue treating elements) project(s) from the carrier.

In some examples of the invention, the selective projection of the excision element is achieved by using the treatment tool of a kind known in the art, where the excision element projects from the carrier body through an opening made along the body portion while moving with respect to the carrier along an axis inclines with respect to the axis LA. In some other examples, the excision element projects from the carrier (e.g. from its distal end) while moving with respect to the carrier substantially along the axis LA. Such configurations are also generally known in the art. The treatment tool may be configured with a removed tissue collecting unit, which may or may not be selectively projectable from the probe.

According to the invention, the medical device is configured such that a dimension of the excision element part projecting from the carrier can be controllably adjusted (varied) in accordance with the determined dimension of the abnormal tissue margins, thereby adjusting the excision volume. Preferably, the excision element is configured for both cutting the tissue and collecting the tissue being cut.

The following are some specific but not limiting examples of the configuration of the device of the present invention. The same reference numbers are used for identifying components that are common in all the examples.

Figure 2:
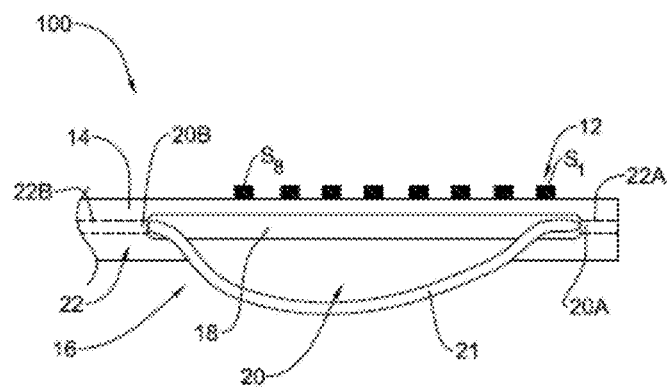
FIGS. 2 to 6 show five examples, respectively, of the device configuration for both the tissue characterization and removal of a tissue specimen.

FIG. 2 shows a medical device 100 for treatment of a tissue specimen, e.g. for removal of an intact tissue specimen. The device 100 includes an elongated shaft/carrier 14 on which sensors $S_1$-$S_8$ of a tissue characterization probe 12 are mounted in spaced-apart locations, and a tissue cutting tool (generally, a treatment tool) 16 mounted on the carrier 14. In this specific not limiting example, the carrier 14 has a hollow body HP (of a cylindrical-like shape) and the treatment tool 16 (cutting tool) is insertable into said hollow body HP.

The cutting tool 16 has a body portion 22 located inside the body HP of the carrier 14, and an excision element 20 projectable from the body 22 through an opening 18 made in the hollow body HP of the carrier 14. In the figure, the excision element 20 is shown in its operative projecting state. The excision element has a cutting edge 21, and may be configured to have a cup-like shape when in the projecting state, thereby enabling collection of tissue while being cut during the rotation of the carrier 14 and thus of the excision element 20.

The excision element 20 extends between its first and second ends 20A and 20B which are attached to respective first and second locations on the treatment tool body 22 and spaced-apart along the axis LA of the carrier 14. The treatment tool is configured to enable a controllable change of the dimensions of the excision element 20. In the present example, this is implemented by making the treatment tool body 22 from two spaced members 22A and 22B, where at least one of them is slidable with respect to the other along the carrier axis LA. As a result, a distance between the first and second locations, and accordingly the first and second ends 20A and 20B of the excision element, changes, thereby enable adjustment of the dimension of the cutting portion 21 projecting through the carrier 14.

By controlling the location of the excision element distal and proximal ends 20A and 20B along the carrier 14, and thus controlling the excision volume, a user can perform optimal removal of a tissue specimen, for example during a breast biopsy procedure. The entire excision element 20 may be movable along the body 22. Thus, the excision volume is controlled by user by changing the location of the excision element 20 along the carrier 14 and changing a distance between the distal and proximal ends of the excision element.

Figure 3:
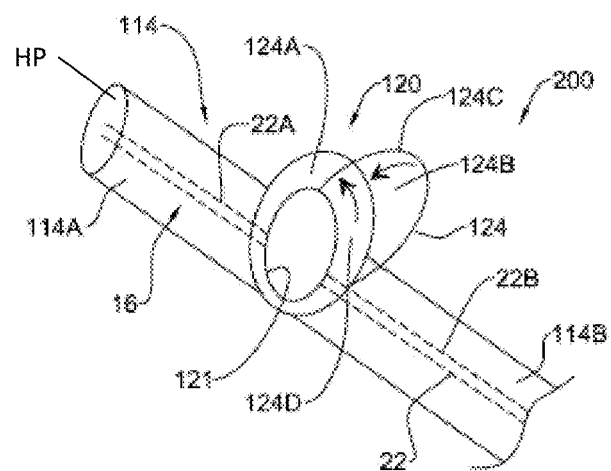

In the above example, the tissue removal procedure is carried while rotating the carrier 14. Such procedure can be performed while keeping the carrier position and rotating the treatment tool. This is exemplified in FIG. 3. A device 200 includes a carrier 114 formed by two separate parts 114A and 114B kept together by a treatment tool 16 inside the carrier 114. The treatment tool 16 has a body part 22 formed by two spaced-apart members 22A and 22B, and an excision element 120 attached thereto by its distal and proximal ends 20A and 20B. The excision element 120 has a semi-spherical surface 124 defining a cutting edge 21. The surface 124 has two arc-like portions 124A and 124B movable along the axis LA such that when they move towards one another one of the portions 124A becomes received by the other portion 124B. Also, the surface 124 has two parts 124C and 124D separately movable such that portion 124C can be received by portion 124C. These movements allow for altering the excision volume when in the operative projecting state of the excision element 120 and for shifting the element 120 between its operative projecting position and its inoperative position being located inside the carrier 14. Cutting is implemented while rotating the tool body 22 with respect to the carrier 14. Also, this configuration allows for collecting the tissue specimen while being cut.

Figure 4:
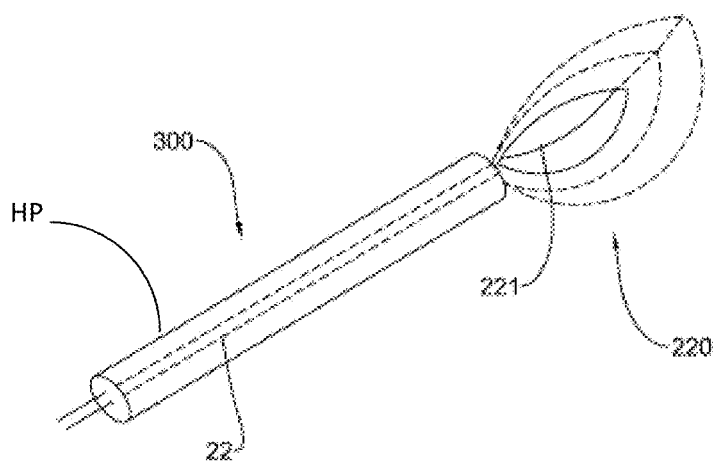

FIG. 4 shows a medical device 300 according to yet another example of the invention. Here, a treatment tool 216 has a body shaft 22 carrying at its distal end an excision element 220. The latter may or may not be integral with the body shaft 22. The excision element has a closed-loop cutting edge 221 which is pre-bent at fabrication so as to deploy from its inoperative closed position when inside the carrier 14 into an open ring-like shape when being projected from the carrier. Attached to the cutting edge 221 is a flexible tissue collecting unit. When the excision element is pushed (by user) out of the carrier 14 through its distal end, it gradually passes through its different operative states being of a spoon-like shape of different dimensions.

Figure 5:
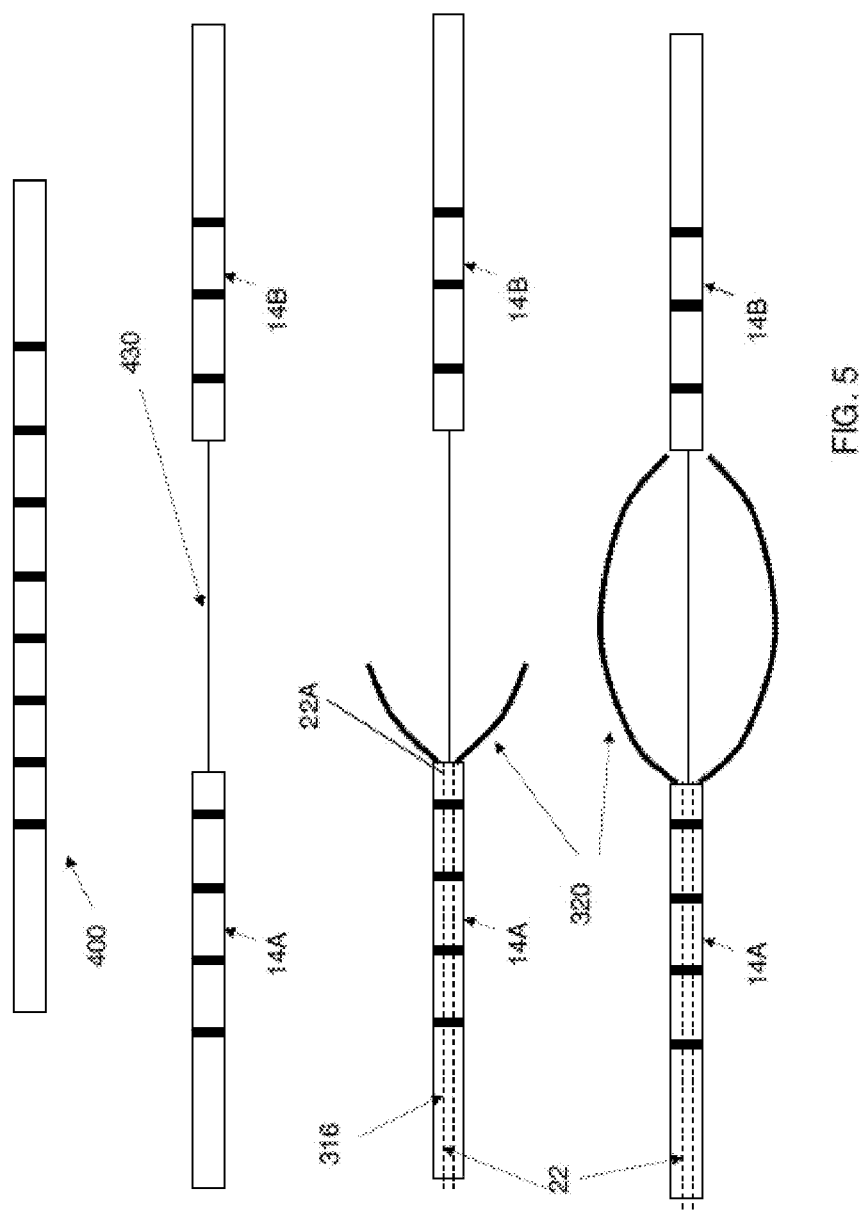

FIG. 5 shows a medical device 400 according to yet another example of the invention. Here, an elongated shaft (carrier) 14 is separable into two sections 14a and 14b, which remain connected to each other by a wire or shaft 430. A treatment tool 316 located inside the carrier 14 has a body shaft 22 carrying at its distal end 22A excision elements 320. The latter may or may not be integral with the body shaft 22. The treatment tool shaft 22 is advanced inside the shaft 14 until its distal end 22A reaches the distal end of the section 14A. Excision elements 220 are then deployed so as to excise an intact tissue portion.

Figure 6:
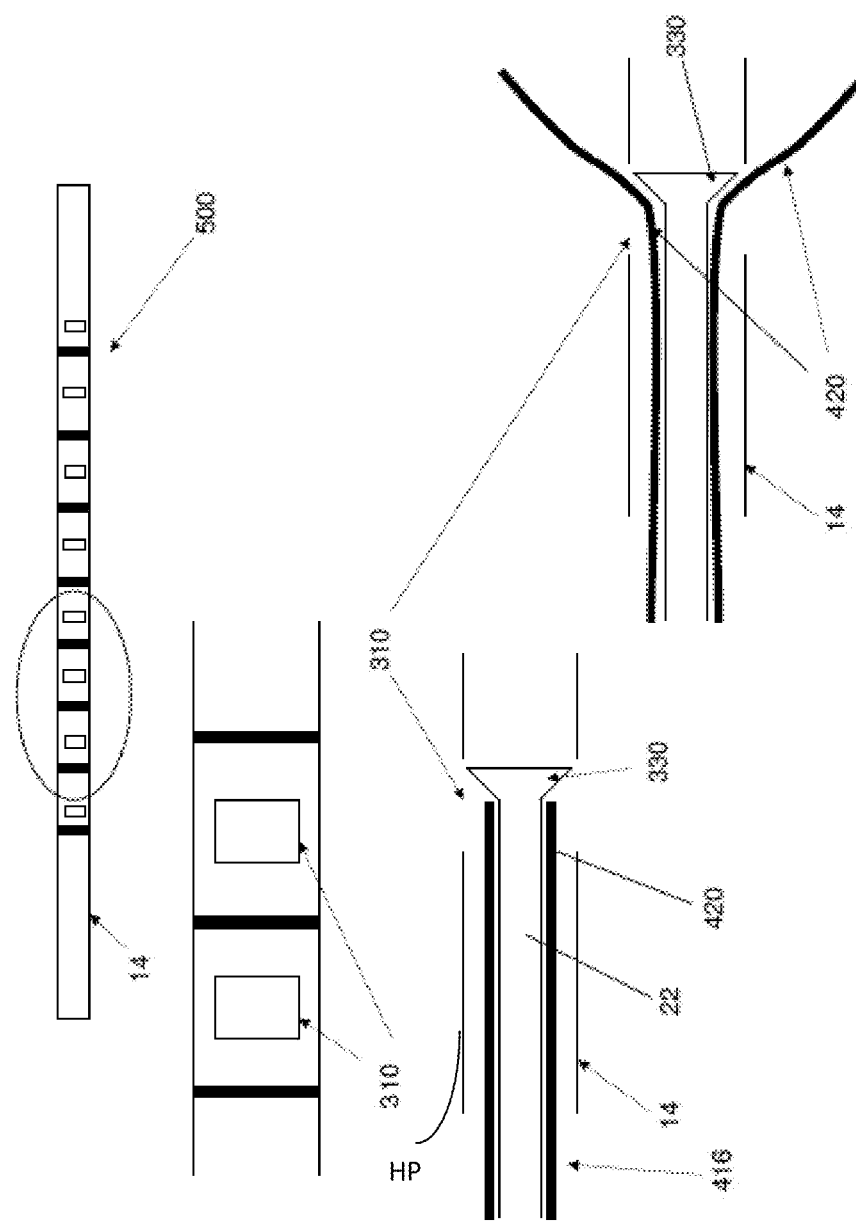

FIG. 6 shows a medical device 500 according to yet another example of the invention. Here, peripheral slots 310 are provided in the shaft/carrier 14 being interspaced between tissue characterization sensors. At each location along the shaft 14 there may be 2-8 peripheral slots. A treatment tool 416 has a body shaft 22 carrying at its distal end excision elements 420. The latter may or may not be integral with the body shaft 22. A number of excision elements 320 corresponds to the number of the slots 310. The treatment tool 416 is advanced inside the shaft 14 until its distal end is positioned at a specific slot 310 location. The distal end of the treatment tool shaft 22 has a tapered/angled ending portion 330. This ending portion allows for controlling an angle at which the excision elements 420 is extended from the shaft 14 into tissue. The excision elements 420 are pre-bent so that when extended they close back on the shaft 14, thus cutting the tissue portion adjacent to the shaft 14. Additionally, the excision elements 420 may be connected at their ends by wires, or other flexible connection. This connection can be manipulated to induce the contraction of the excision elements 420 towards shaft 14, to facilitate cutting of the tissue portion adjacent to the shaft 14.

Reference is now made to FIGS. 7A-7E which show more specifically some exemplified features of the invention. A medical device 600 is shown which is configured for use in tissue characterization and treatment, and includes a tissue characterization probe 12 carried by an elongated shaft/carrier 14 and is configured for carrying a treatment tool 610. The carrier 14 has distal and proximal ends 14A and 14B, and has two integral portions, i.e. a hollow portion HP (of a cylindrical-like shape) extending from proximal end 14B and a trough-like portion (or an open-cut portion) 14D extending from said hollow portion towards the distal end 14A. As will be described below, the treatment tool when attached to/mounted on the medical device is at least partially located inside the hollow portion HP and either permanently or selectively (when required) projectable from the hollow portion HP such that a part of the treatment tool extends along the trough portion 14D to be exposed to the tissue. The hollow portion HP may have a thin wall configuration, so it does not add any remarkable thickness to the treatment tool passing through it, which in turn enhances the convenience in using and inserting the device 600 into a subject's body. The tissue characterization probe 12 includes an array of spaced-apart tissue characterization sensors, generally at S. The sensors are located on an external side (bottom side) of the trough portion 14D (there may be additional sensors extending along the hollow portion, as will be described herein below), while the opposite, internal side of the trough portion 14D serves as a site for locating a portion of the treatment tool while in an operative position thereof.

As shown in the non-limiting example of FIGS. 7A1-7A2, the sensors extend along the trough portion 14D, and may be arranged in a one-dimensional array extending along the longitudinal axis of the carrier 14. FIGS. 7B1-7B2 show side and bottom views of another possible not limiting example of the configuration of the medical device 600. The device 600 includes a tissue characterization probe 12 having an elongated shaft/carrier 14 configured for carrying the treatment tool (610 in FIGS. 7C-7E). The carrier 14 has two integral portions, i.e. a hollow portion HP (of a cylindrical-like shape) extending from proximal end 14B of the carrier and a trough-like portion (or an open-cut portion) 14D extending from said hollow portion towards the distal end 14A of the carrier. The tissue characterization probe 12 includes two groups of sensors S, one group 12A being located on the trough-like portion 14D and being arranged for example as a one-dimensional array of spaced-apart tissue characterization sensors, and the other group 12B of sensors extending along the hollow portion HP and including a two-dimensional array of sensors covering the whole or part of the carrier's circumference. The provision of sensors along the hollow portion HP may be very helpful in the monitoring and characterization process may guide the operator and give indication of how large the tissue to be treated by the treatment tool 610 is, thereby saving time and enhancing the patient convenience.

It should be noted that the sensors may be thin, and thus do not protrude too much from the outer surface of the carrier/trough's part 14D, consequently further enhancing the effectiveness and convenience in using the device inside the subject's body. As mentioned above, such thin and possible flexible sensor structures are described for example in WO 2011/016035, which is assigned to the assignee of the present application and which is incorporated herein by reference. According to this technique, a sensor unit/structure includes a near field electromagnetic sensor and a flexible signal transmission structure, which are integral with one another by means of one or more common continuous surfaces. The flexible signal transmission structure may be constructed from a first layer including signal connection lines associated with sensor cells of the near field electromagnetic sensor and a second electrically conductive layer electrically coupled to the electrically conductive material of the sensor.

It should be understood that the treatment tool portion may or may not be physically supported by the internal side of the trough portion 14D. Thus, the treatment tool portion, and accordingly a tissue segment accessed by the treatment tool, can be concurrently aligned with the sensors, enabling the treatment procedure to be carried out without a need to displace the sensing portion of the device. Thus, at least part of the array of sensors is located at the distal part 14D of the elongated shaft 14, and this distal part 14D forms the trough portion of the device which concurrently exposes both the sensors and the treatment tool to the same part/segment of the tissue. It can be appreciated that the device 600 enables immediate treatment or acquisition of very small tissue mass at the exact location of any one of the sensors, during scanning of a tissue mass and without any need for moving the sensors from place as may be required with the above-described device 400 for example.

As shown in FIGS. 7C-7E, the device 600 may include a tissue cutting tool 610 (constituting a treatment tool) being carried and housed inside the proximal hollow portion HP of the shaft 14 and projecting therefrom and extending above the distal, trough portion 14D. The shaft 14 and the cutting tool 610 mounted therein can move forwards and backwards relative to each other. The excision element 612 (constituting a treatment tool portion) of the cutting tool 610 is in its operative position when it is located above the trough part 14D or at least partially extends beyond it forwardly into the tissue mass being treated. It should be noted that any suitable cutting tool that conforms to the shape and dimensions of the carrier 14 can be used and the invention is not limited to the cutting tool 610 being shown in this specific example, and any other cutting tool as well as any other treatment tools can be used, such as a tool for delivering treatment medication.

The device 600 is typically configured as a hand-held device having a handle portion 630 at the proximal end 14B of the carrier 14 (FIG. 7B). Further, the device 600 may include a movement mechanism located at the proximal end 14B of the carrier 14, enabling relative displacement between the carrier 14 and the treatment tool 610. The movement mechanism may be manually activated by user and/or may be assisted by a motor unit 640. The movement mechanism (e.g. the motor unit) may be mounted inside the handle.

The motor unit 640 drives a movement of the carrier/shaft 14 relative to the treatment tool (cutting tool) 610 forwards and backwards as shown in FIGS. 7E and 7D, allowing for covering, revealing or repositioning the cutting tool 610 during the treatment process. FIGS. 7D and 7E exemplify two different relative positions of the carrier and the treatment tool. In this specific but not limiting example, the configuration is such that the carrier 14 moves with respect to the treatment tool 610. In the example of FIG. 7D, the carrier 14 is in its retracted position (retracted towards the handle) exposing a longer portion of the treatment tool to the tissue mass, as compared to the extracted position of the carrier 14 shown in FIG. 7E, where a shorter portion of the tissue tool is exposed.

Possibly, the movement mechanism (either manual or driven by motor) includes a registration assembly to define a reference/registration position for the sensors' array with respect to a reference plane, which may be defined by the handle location. This assists in accurate determination of the dimension of an abnormal tissue specimen that is to be treated. The registration assembly may be formed by an L-like shaped bracket which by its one arm L1 of a given length is movably (telescopically) connected to the handle 630 and by its other arm L2 is connected to the carrier. Thus, when the arm L1 moves towards and away from a reference plane RP defined by the distal edge of the handle 630 (via a respective guiding mechanism which is not specifically shown) between its refracted and extracted positions with respect to the handle, the carrier 14 becomes correspondingly movable towards and away from the handle. Such configuration assists in monitoring the sensors' repositioning caused by the movement of the carrier which is in turn controlled by the movement of the bracket 620 with respect to the reference plane RP. It should be noted, that the reference plane RP can be defined at another point along the device, and it is not limited to the shown in FIGS. 7D-E, in any case the calculations of distances are adapted to the reference plane chosen.

In some embodiments, the registration assembly of the movement mechanism may include a sensing unit 642 illustrated in FIG. 7D (e.g. imaging unit, electro-optic sensor, magnetic sensor) which dynamically identifies the position of the sensors array relative to the reference plane RP or to another reference point/position and delivers real-time position data to a control unit that can be located in the handle 630 or outside the medical device or to the control system 19. Alternatively, the sensing unit may be located on carrier 14 or bracket 620.

The movement mechanism of the invention may include a locking system, being mechanical, electrical or electro-mechanical, that has the ability to maintain the sensor array 12, carried by the carrier 14, at fixed and locked positions relative to the treatment tool 610. The provision of lock positions enables during an invasive procedure to reduce/overcome the friction forces applied by the body tissues on the medical device. If the movement of the carrier 14 is continuous, the locking system can be actuated at any point along the moving part (e.g. the carrier 14). Alternatively if the movement of the carrier 14 occurs in defined steps having known distance (generally in millimeters), the locking system can be activated at those defined steps. For example, the proximal end 14B of the carrier 14 which is located inside the handle 630 may include a toothed part along the longitudinal axis that engage another toothed part of an adjacent suitable member. The step of the tooth defines the movement steps.

Figure 8A:
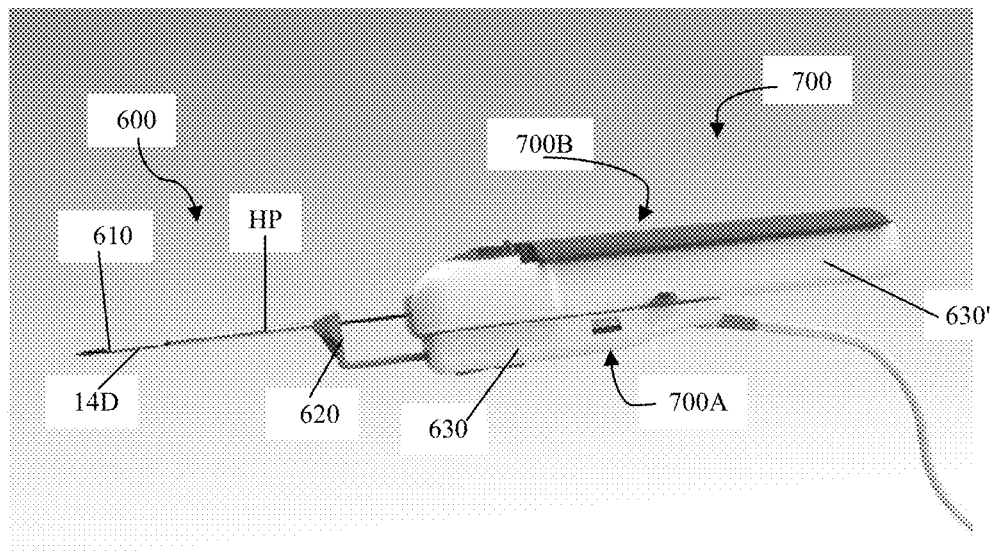
FIGS. 8A-8B show one configuration of a tissue treatment apparatus utilizing the medical device of the present invention.
Figure 8B:
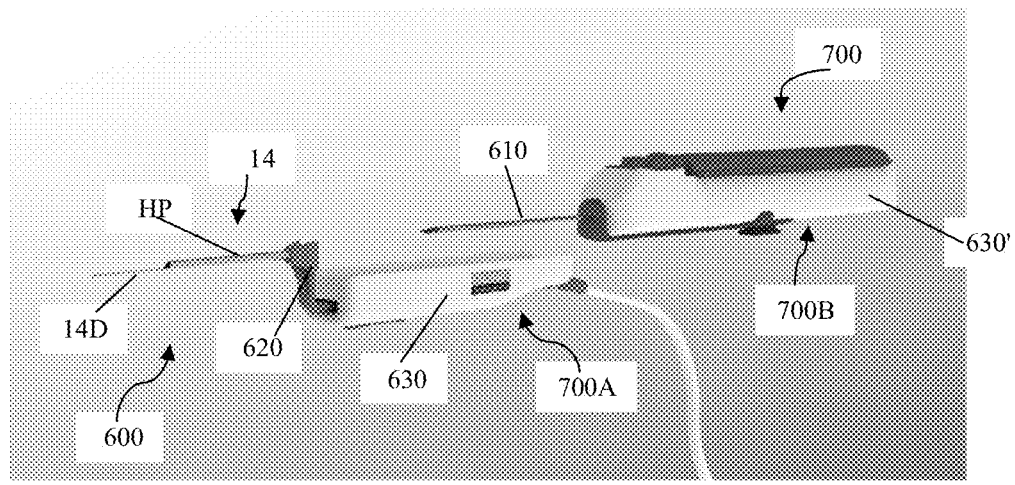
Figure 9:
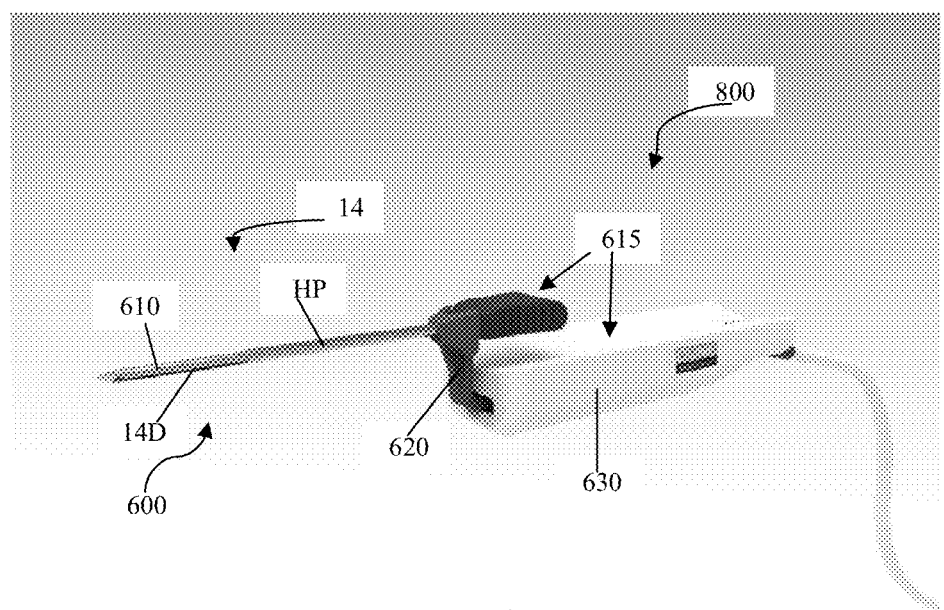
FIG. 9 shows a second configuration of a tissue treatment apparatus utilizing the medical device of the present invention.

In general, the movement mechanism is configured to provide mechanical support to the relative movement between the carrier 14 and the treatment tool 610, and at the same time to preserve electrical signal transfer between the sensors and the control unit (transmitter/receiver) which may be located outside the hand-held device. In this specific example of device 600, there is a rigid connection between the bracket 620 and the carrier 14 which provides for the mechanical support. Inside the handle 630 there is a movement mechanism configured as described above. It should be noted, although not specifically shown that in order to maintain the electrical connectivity between the sensors and a control unit located inside or outside the handle 630, proper connection arrangement is provided. This may be achieved by using a flexible transmission structure configured as described in the above mentioned WO 2011/016035 which is assigned to the assignee of this application and is incorporated herein by reference. Alternatively, an electrical connector may include a rigid portion connecting the sensors to a certain location on the part L1 of the bracket 620, and a generally flexible cable that connects said location on the part L1 of the bracket 620 to a location on an electronic panel inside the handle to which the signals from sensors are to be delivered, thus allowing back and forward movement of the carrier 14 while providing electrical signal transfer irrespective of the movement. Reference is now made to FIGS. 8A-8B and 9 showing two different configurations of a tissue treatment apparatus utilizing the medical device of the present invention.

In the example of FIGS. 8A-8B, the apparatus, generally designated 700, is configured as a two-part assembly. As better seen in FIG. 8B, the device 600 carrying the tissue characterization probe of the invention is associated with part 700A, while a treatment tool is carried by the part 700B. More specifically, the tissue characterization device 600 is mounted on a handle 630, e.g. via the registration assembly 620, and the treatment tool 610 is mounted on a handle 630'. The two parts 700A and 700B are configured to engage with one another as shown in FIG. 8A. The engagement is implemented by insertion of the treatment tool 610 into the hollow portion HP of the carrier 14 (FIG. 8B) and in the engaged position the handles 630 and 630' are aligned with one another. A suitable locking mechanism may be provided (not shown) securing the engaged position of the handles 630 and 630' during the apparatus operation thus allowing only the movement of the carrier 14 via the movement of the bracket 620 as described above. It should be noted that the device 600 of the invention may be designed (i.e. the carrier 14) so as to match the configuration of a suitable/desired treatment tool.

In the example of FIG. 9, the tissue treatment apparatus, designated 800, includes the above-described tissue characterization device 600 which in this specific but not limiting example is mounted on a handle 630 via a bracket 620 associated with an appropriate movement mechanism 615 (which may be manual, automatic, or a combination of both). The bracket 620 may be movable with respect to the reference plane defined by the distal edge of the handle causing a controllable movement of the carrier 14 with respect to the treatment tool 610.

It should however be noted that for some applications, e.g. in sterile conditions or for disposable usage, the treatment apparatus described may not use any handle and thus may be formed solely by the device 600 (i.e. the carrier 14 configured as exemplified above) and bracket 620. Alternatively, bracket 620 may be configured so as to enable connection and disconnection of bracket 620 from the handle 630. This also allows the device 600 (i.e. the carrier 14 configured as exemplified above) and bracket 620 to be disposable and/or sterile one.

The movement mechanism used in the invention may be configured to suit different applications, and its implementation may be influenced by several factors, e.g. the force needed in order to move the carrier relative to the treatment tool during an invasive procedure, the preferred speed of the movement, the accuracy of the movement and others. In the following, more examples of medical apparatuses that contain movement mechanisms having different configurations are presented.

Figure 10A:
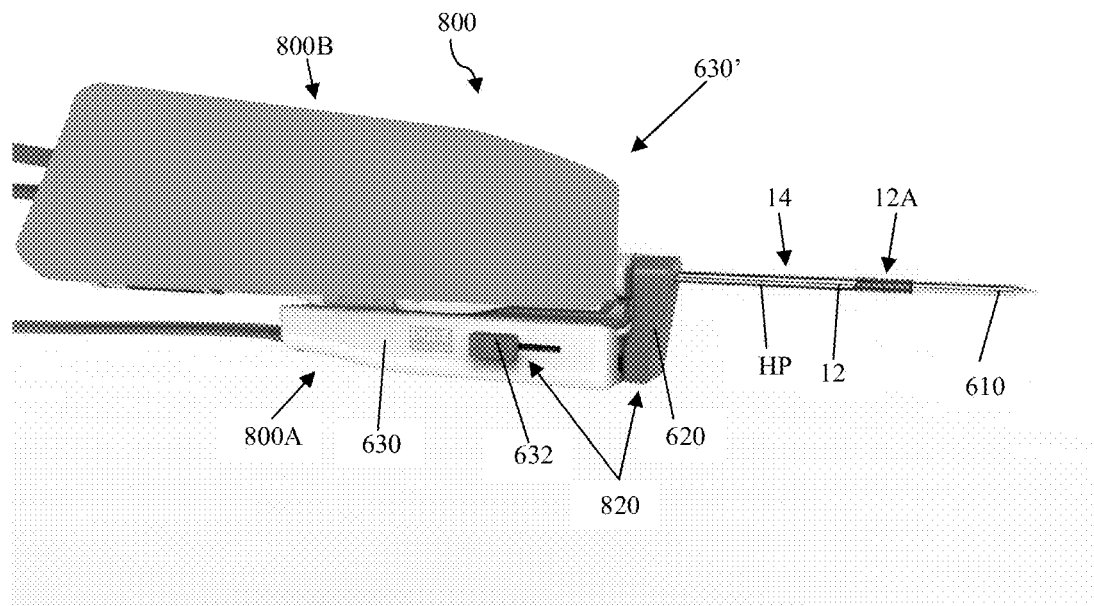
FIGS. 10A-10B show an example of a tissue treatment apparatus and a movement mechanism utilizing the medical device of the present invention.
Figure 10B:
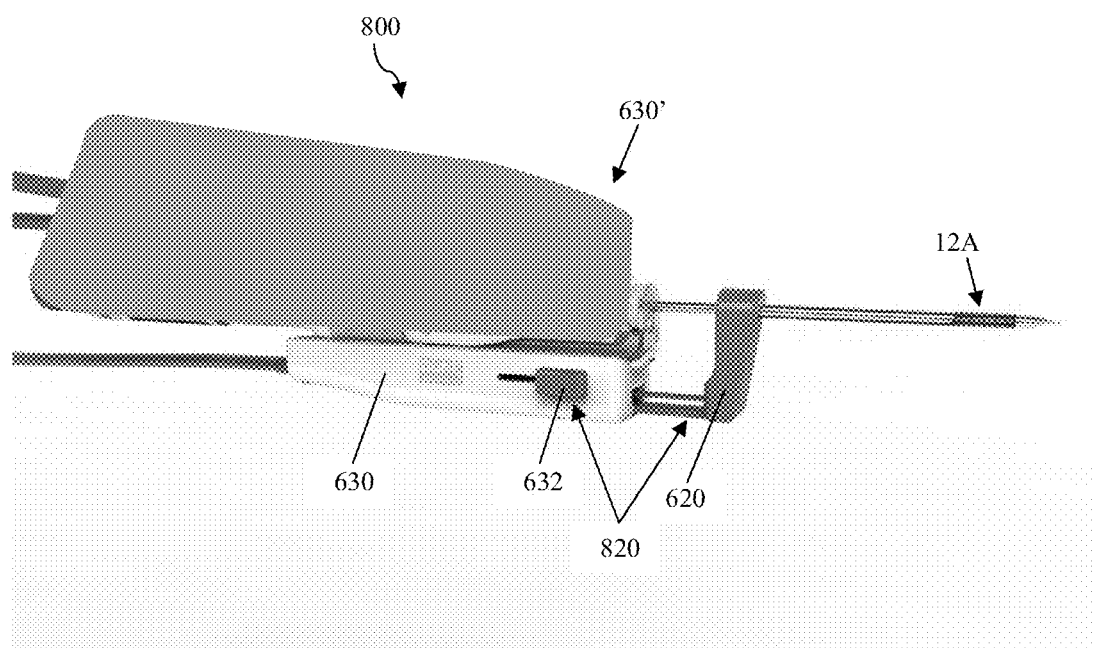

FIGS. 10A-10B show one example of an apparatus 800 including a specific and non-limiting arrangement of a movement mechanism 820. In this specific and non-limiting example, the apparatus generally designated 800 is configured as a two part-assembly. The device carrying the tissue characterization probe 12 such as the probe in FIG. 1B is associated with part 800A, while a treatment tool 610 is carried by the part 800B. More specifically, the tissue characterization device is mounted on a handle 630, e.g. via the bracket 620, and the treatment tool 610 is mounted on a handle 630'. The two parts 800A and 800B are engaged together and the treatment tool 610 is passed through the probe 12 to form the apparatus 800.

The probe 12 may include an array of sensors 12A as described above with respect to FIG. 1B. This array of sensors might be configured according to the arrangements disclosed in WO 2011/016035, and may include a signal transmission structure attached to the probe 12. The structure connects the sensors to a control unit located inside the handle 630 or outside the apparatus.

The apparatus also include a registration assembly. As described above, the registration assembly may be formed by an L-like shaped bracket 620 which by its one arm of a given length is movably (telescopically) connected to the handle 630 and by its other arm is connected to the carrier 14.

In the specific example described in FIGS. 10A-10B, the movement mechanism 820 includes the bracket 620 and a slider 632 configured to generate movement of the shaft 14 relative to the treatment tool (cutting tool) 610 forwards and backwards, the treatment tool 610 being between its inoperative position being located substantially entirely inside the hollow portion of the carrier and its operative position projecting by its treating portion towards outside the carrier. The slider 632 may be located on one side of the handle 630 or on both sides. Moving the slider 632 forwardly as illustrated in FIG. 10B causes the bracket 620 and the probe 12 attached to the bracket to move forwardly relative to the treatment tool 610 (and covering the front active part of the treatment tool). Moving the slider 632 backwardly to its back position, as shown in FIG. 10A, slides the bracket 620 and the probe 12 back exposing a longer part of the treatment tool's front side, including the excision element 612. The sliding of the slider 632 may be continuous or by defined pitches that result in known displacements of the carrier 14; increasing the control and the convenient operation of the medical device.

Another not limiting example of a treatment apparatus 900 according to the present invention is shown in FIGS. 11A and 11B. The apparatus is also configured as a two-part assembly. The device 600 carrying the tissue characterization probe of the invention is associated with the lower part 900A, while a treatment tool is carried by the upper part 900B. The apparatus 900 has the same features of the apparatus 700 in FIG. 8A apart from a different movement mechanism 920. The movement mechanism 920A is manual and is associated with a bracket 620A. The bracket 620A has an upper region 622A and a lower region 624A. During operation, the upper region 622A or lower region 624A or both (depending on the apparatus's orientation) can be pushed by the user forwardly, thus moving the hollow part of the carrier 14 that is attached to the bracket 620A forwardly, thereby covering the front active part of the treatment tool 610. The user can then move the carrier 14 backwards towards the part 630' to expose the treatment tool as needed by manually pushing the bracket 620A backwardly. The languet element 626A forming the lower part of the L-shape registration assembly enters the part 630 and maintains the balanced straight movement of the carrier 14. The distal part languet element 626A serves as an interlock that limits the outward movement of the carrier 14.

The apparatus 910 may include a movement mechanism 940 associated with another bracket configuration such as the bracket 620B, as shown in FIGS. 12A and 12B. In this specific not limiting example, the movement mechanism 940 is manual and utilizes two lateral arms 622B which can be pushed forwardly by the user causing the covering the front active part 610 of the treatment tool by the carrier 14. On the other side, pushing the region 620Bo of the bracket 620B retracts the carrier 14 to expose the front active part 610 of the treatment tool. The choice of bracket, 620A or 620B, may depend on the effectiveness and/or convenience of operation which might be affected, inter alia, by the part of body being treated.

Figures 13A, 13B:
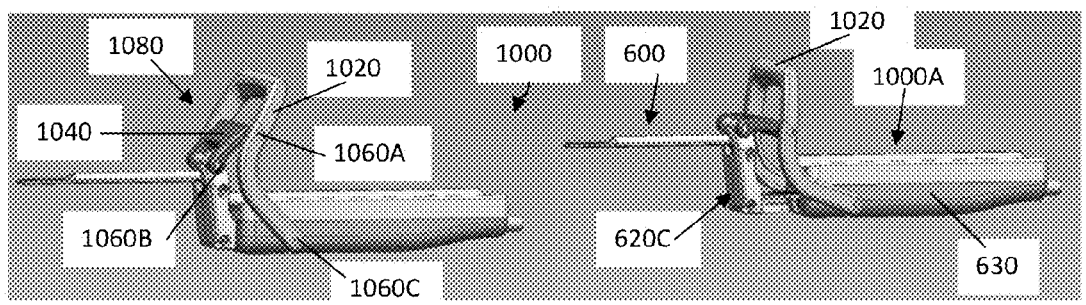
FIGS. 13A-13B show an example of a lower part of a tissue treatment apparatus using the medical device of the present invention.

Referring to FIGS. 13A-13B, another example of an apparatus 1000 according to the present invention is shown. Here, only the part 630 associated with a lower part 1000A of the apparatus 1000 and including the tissue characterization device 600 is shown. The second upper part of the assembly associated with the treatment tool 610 is not shown and is similar to anyone of the previously shown apparatus's upper parts such as 700B, 800B and 900B. The movement mechanism 1080 (integrated with the part 1000A) is manual and utilizes a handle 1020, an intermediate platelet 1040, connecting hinges 1060A-B-C and an L-shape bracket 620C. As shown in the figures, the handle 1020 is connected by its lower side to the lower part 630 of the apparatus via the hinge 1060C, and to the platelet 1040 via the hinge 1060A. The platelet is connected through its opposite side to the top side of the bracket 620C via the hinge 1060B. FIG. 13A shows the handle 1020 in its retracted position, i.e. when the tissue characterization device 600 is kept closer to the apparatus, thus exposing the front active part of the treatment tool. The handle 1020 is configured and operable to be pushed forwardly, as shown in FIG. 13B, causing the relative motion of the platelet 1040 and the bracket 620C forwardly and covering the front active part of the treatment tool by the carrier 14. This motion is enabled and governed by the connecting hinges 1060A-B-C. The special configuration of the movement mechanism 1080 in the apparatus 1000 enables the application of larger forces in comparison to the forces that can be applied in the previously presented system 900. However, the system 900 may be preferable when a more sensitive and smaller force is needed. Accordingly, when dealing with parts of the body that require the application of such large forces during the treatment procedure, the system 1000 might be used.

Figure 14A:
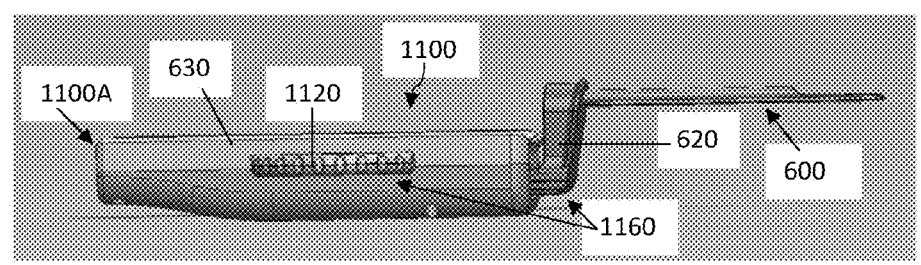
FIGS. 14A-14E show an example of a tissue treatment apparatus and a movement mechanism having another configuration utilizing the medical device of the present invention.
Figure 14B:
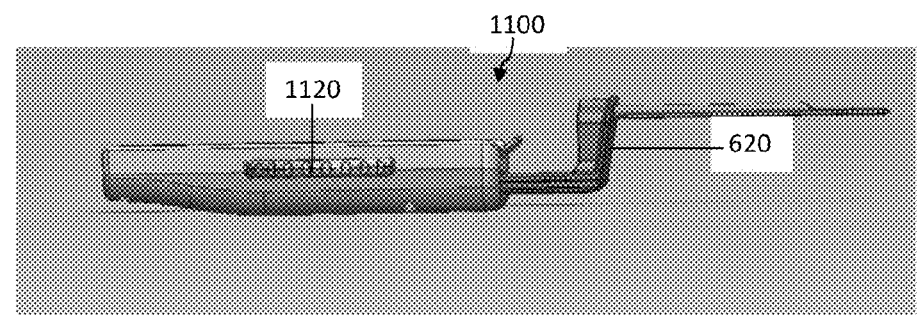
Figure 14C:
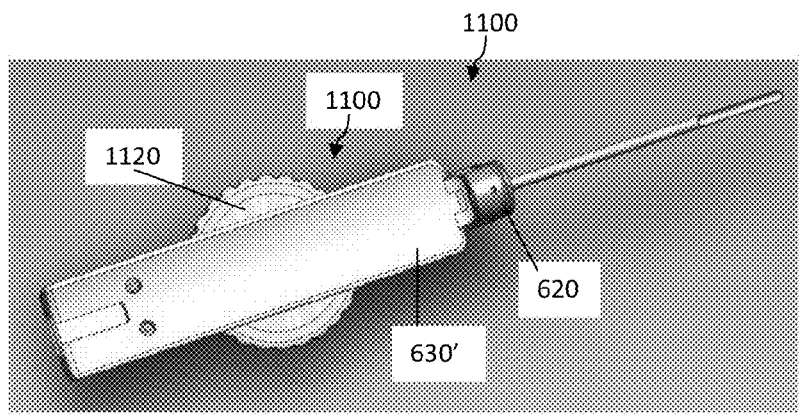
Figure 14D:
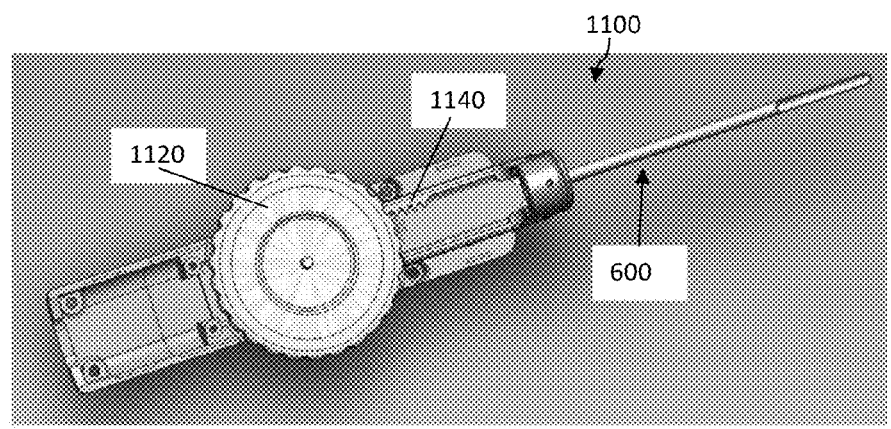
Figure 14E:
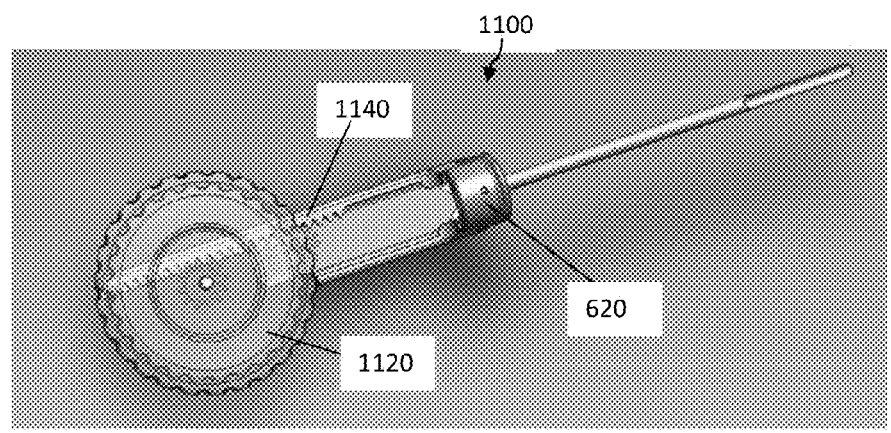

Reference is now made to FIGS. 14A-14E showing another medical apparatus 1100 utilizing the tissue characterization device 600 of the present invention. The apparatus 1100 is similar to the previous described devices 900 and 1000 and have a two-part assembly configuration, where the upper part is associated with the treatment tool and the lower part is associated with the tissue characterization probe 600. FIGS. 14A and 14B are side views of the retracted and the extracted positions of the bracket 620 (and probe 600) respectively, FIGS. 14C-14E are top views of the lower part 1100A of the apparatus 1100. Here, the movement mechanism 1160 includes a circular gear 1120 (called "pinion") associated with a linear bar 1140 (called "rack"). As shown, the pinion 1120 and the rack 1140 both have their teeth engaged, so that rotation of the pinion 1120 by the user translates into linear motion of the rack 1140. The rack 1140 is fixedly attached to the bracket 620, so when the rack 1140 moves forwardly and backwardly, the bracket 620 and the device 600 will also move forwardly and backwardly.

Figure 15A:
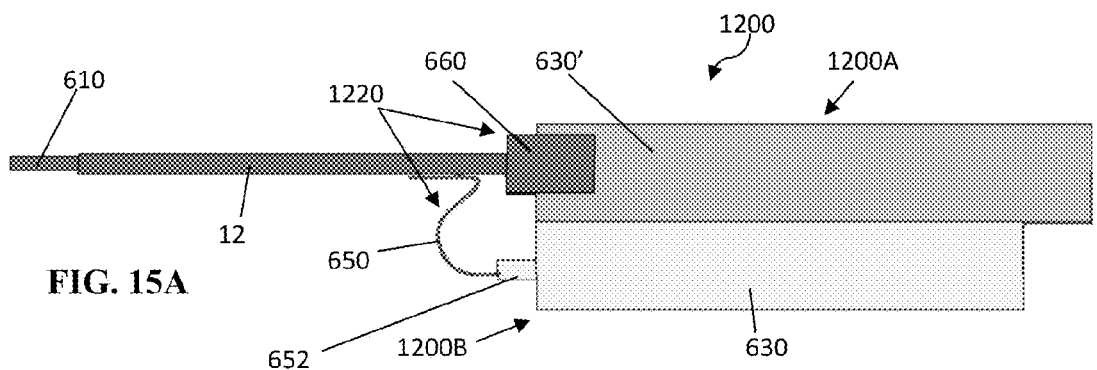
FIGS. 15A-15C illustrate an example of a tissue treatment apparatus utilizing the medical device of the present invention.
Figure 15B:
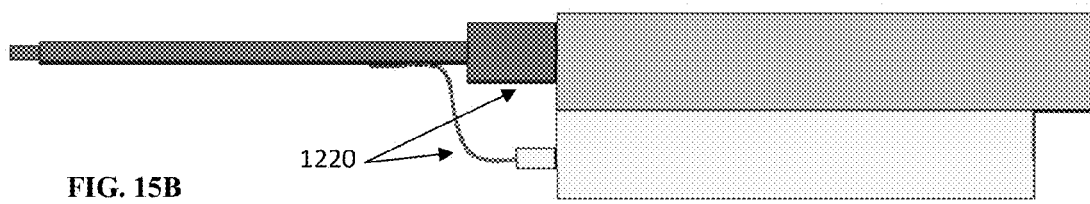
Figure 15C:
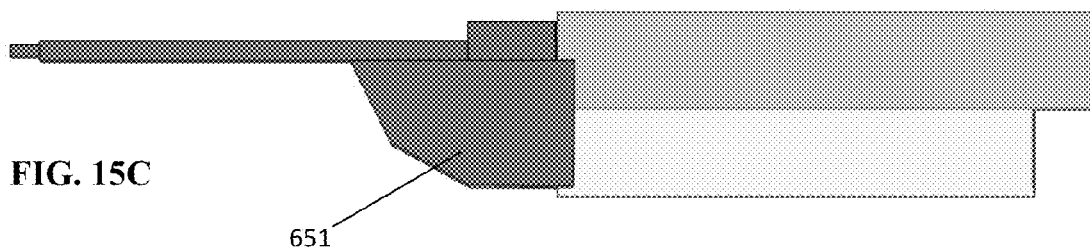

In FIGS. 15A-15C, a schematic illustration of one more possible embodiment according to the present invention is shown. This embodiment emphasizes the use of the flexible transmission lines described in WO 2011/016035. An apparatus 1200 includes two parts 1200A (upper) and 1200B (lower) engaged together. The treatment tool 610 is fixedly attached to the upper part 1200A. The proximal side of the tissue characterization probe 12 (alternatively device 600) is securely attached to a base 660 connectable to the part 1200A, possibly the handle 630'. The base 660 and the probe 12 (or 600) surround the treatment tool 610. The movement mechanism 1220 is configured to enable the forward and backward movement of the base 660 and of the probe 12. The movement mechanism 1220 utilizes a manual, automatic or hybrid actuation scheme. A sensor array mounted on the probe 12 (not shown) is connected via a flexible transmission line structure 650 that maintains, irrespective of the motion between the probe 12 and handle 630, the steady electrical transmission of the signals from the sensors to a rigid connector 652 located at the front side of the handle 630, the signals are then carried from the connector 652 via one or more suitable cables to a control unit located either inside or outside the handle 630.

In FIG. 15A, the probe 12 is in its refracted position exposing a long portion of the front part of the treatment tool to the tissue mass relatively to the length of the treatment tool.

In FIG. 15B, the probe 12 is in its extracted position covering a long portion of the front part of the treatment tool relatively to the length of the treatment tool.

The transmission structure 650 is configured and chosen such as to allow this situation by providing it with enough length.

In FIG. 15C a protective cover 651 placed beside the handle 630 and under the probe 12 is shown. The protective cover 651 protects the transmission line structure.

It should be understood that in all the above-exemplified embodiments the device may be rotated, manually or mechanically, to assist in complete tissue treatment (e.g. cutting and removal). The removal/acquisition of relevant tissue portion may be carried out manually or by using a suctioning mechanism possibly implemented in the apparatus, e.g. in the handle 630'. The removed tissue is suctioned through the portion HP of the carrier 14 and out of the body, to be further treated as desired.

Thus, the present invention provides a novel medical device capable of precisely locating a tissue volume to be treated (removed), and also provides for treating (removing) the tissue by an integral treatment tool.

The invention claimed is:

1. A medical device for use in characterization and treatment of a tissue mass, comprising:

a carrier in the form of an elongated hollow shaft having a rigid cylindrical shape extending along a longitudinal axis and open proximal and distal ends, and a plurality of tissue characterization sensors mounted on at least part of a surface of the shaft and arranged in a spaced-apart relationship with known distances between the tissue characterization sensors, wherein at least some of said plurality of sensors are arranged in a two-dimensional array along both the longitudinal axis and at least part of a lateral axis of said shaft, such that during movement of the shaft along the longitudinal axis through the tissue mass each of the sensors generates tissue characterization signals from successive locations of the sensor within the tissue mass, and such that at each position of the shaft inside the tissue mass said at least some of plurality of sensors concurrently generate tissue characterization signals from locations surrounding the shaft along both the longitudinal and lateral axes, thereby enabling to locate and determine dimensions of an abnormal tissue inside said tissue mass.

2. The device according to claim 1, wherein the plurality of tissue characterization sensors are arranged in at least one circular portion along a circumference of the shaft.

3. The device according to claim 1, wherein said shaft has two integral portions including a distal portion and a hollow portion extending between the proximal end of the shaft and said distal portion, said shaft being configured for passing a treatment tool through the hollow portion and enabling at least a part of the treatment tool to project from the hollow portion and extend along the distal portion, the device thereby enabling consequent treatment of a tissue specimen by the treatment tool.

4. The device according to claim 3, wherein said distal portion is configured as a trough like member thereby enabling concurrent alignment of a distal portion of the treatment tool at one side of the distal portion and the plurality of tissue characterization sensors at opposite side of the distal portion to the same segment of the tissue mass.

5. The device according to claim 4, wherein said plurality of tissue characterization sensors comprise sensors arranged along the circumference of the hollow portion and sensors arranged along an axis of the trough like member.

6. The device according to claim 1, comprising a treatment tool carried by said shaft.

7. The device according to claim 1, further comprising a handle, wherein the handle and the shaft are configured to be removably connectable to each other at the proximal end of the shaft, such that the handle extends proximally from the proximal end of the shaft.

8. The device according to claim 7, wherein the handle is configured for fixedly engaging with a handle portion of a treatment tool when the treatment tool is being inserted into a hollow portion of the shaft.

9. The device according to claim 6, comprising a movement mechanism located at the proximal end of the shaft, and being configured and operable to enable relative displacement between the shaft and the treatment tool.

10. The device according to claim 7, comprising a movement mechanism located inside the handle, and being configured and operable to enable relative displacement between the shaft and the treatment tool.

11. The device according to claim 6, comprising a movement mechanism enabling relative displacement between the shaft and the treatment tool, wherein the movement mechanism comprises a registration assembly to define a reference position for the plurality of tissue characterization sensors with respect to a certain reference plane defined by the device, thereby enabling to monitor repositioning of the plurality of tissue characterization sensors caused by movement of the shaft with respect to the reference plane.

12. The device according to claim 11, wherein said registration assembly comprises a sensing unit configured and operable to identify a position of the two-dimensional sensor array relative to said reference plane and to generate data indicative thereof.

13. The device according to claim 10, wherein the movement mechanism comprises a registration assembly to define a reference position for the plurality of tissue characterization sensors with respect to a certain reference plane defined by the handle.

14. The device according to claim 13, wherein the registration assembly comprises an L-like shaped bracket, a first arm of a given length of the L-Like shaped bracket is movably connected to the handle and a second arm of the L-Like shaped bracket is fixedly connected to the shaft, the reference plane being defined by a distal edge of the handle, thereby enabling to monitor repositioning of the plurality of tissue characterization sensors caused by movement of the bracket with respect to the reference plane.

15. The device according to claim 10, wherein said movement mechanism comprises a locking system configured to maintaining said plurality of sensors at fixed and locked positions.

16. The device according to claim 10, wherein said movement mechanism comprises a slider configured to selectively displace the treatment tool between inoperative and operative positions.

17. The device according to claim 10, wherein said movement mechanism is configured to convert a rotational movement into a linear relative displacement between the shaft and the treatment tool.

18. The device according to claim 10, wherein said movement mechanism comprises rack and pinion configuration.

19. The device according to claim 1, being configured as a two-part assembly comprising a first assembly and a second assembly, the first and second assemblies being removably attachable to one another.

20. The device of claim 19, wherein said first assembly carries a tissue characterization probe and said second assembly carries a treatment tool.

21. The device of claim 19, wherein said tissue characterization probe and said treatment tool are both carried by said first assembly or said second assembly respectively.

22. The device of claim 1, comprising a control unit configured for receiving and analyzing tissue characterizing signals from each of the plurality of sensors and utilizing data indicative of the respective sensors' locations for determining a dimension of an abnormal tissue specimen, thereby enabling consequent treatment of the abnormal tissue specimen by a treatment tool.

23. The device according to claim 22, wherein the control unit comprises a graphical user interface configured for presenting information related to the signals received from all of the plurality of sensors, thereby providing an operator with information regarding the tissue type at the locations of the plurality of sensors, and facilitating analysis of the location and extent of the tissue to be treated.

24. The device according to claim 1, wherein said plurality of the tissue characterization sensors are coupled to a flexible signal transmission structure by at least one common continuous surface.

25. A medical device for use in characterization and treatment of a tissue mass, comprising a carrier in the form of an elongated hollow shaft having a rigid cylindrical shape extending along a longitudinal axis and open proximal and distal ends, and
   a plurality of tissue characterization sensors mounted on a surface of the shaft within at least a distal portion of the shaft, said tissue characterization sensors being arranged in a spaced-apart relationship with known distances between the tissue characterization sensors, thereby enabling to locate and determine dimensions of an abnormal tissue inside a tissue mass during movement of the shaft along the longitudinal axis through the tissue mass based on tissue characterization signals from the array of sensors; and
   a handle configured to be removably connectable to the shaft at the proximal end of the shaft, such that the handle extends proximally from the proximal end of the shaft.

26. The device according to claim 25, further comprising a movement mechanism configured and operable to enable displacement between the shaft and the handle.

27. The device according to claim 26, wherein the movement mechanism comprises a registration assembly to define a reference position for the array of tissue characterization sensors with respect to a certain reference plane defined by the device, thereby enabling to monitor repositioning of the tissue characterization sensors caused by movement of the shaft with respect to the reference plane.

28. The device according to claim 27, wherein said registration assembly comprises a sensing unit configured and operable to identify a position of the plurality of sensors relative to said reference plane and to generate data indicative thereof.

29. The device according to claim 26, wherein the movement mechanism comprises a registration assembly to define a reference position for the array of tissue characterization sensors with respect to a certain reference plane defined by the handle, thereby enabling to monitor repositioning of the plurality of tissue characterization sensors caused by movement of the shaft with respect to the reference plane.

30. The device according to claim 29, wherein the registration assembly comprises an L-like shaped bracket, a first arm of a given length of the L-like shaped bracket is movably connected to the handle and a second arm of the L-like shaped bracket is fixedly connected to the shaft, the reference plane being defined by a distal edge of the handle, thereby enabling to monitor repositioning of the plurality of tissue characterization sensors caused by movement of the bracket with respect to the reference plane.

31. The device according to claim 30, wherein said movement mechanism has at least one of the following configurations: (i) comprises a locking system configured to maintaining said plurality of sensors at fixed and locked positions; (ii) comprises a slider configured to selectively displace the treatment tool between inoperative and operative positions; (iii) is configured to convert a rotational movement into the linear relative displacement between the shaft and the treatment tool; and (iv) said movement mechanism comprises rack and pinion configuration.

32. The device according to claim 26, wherein said movement mechanism is located inside said handle.

33. The device according to claim 32, further comprising a treatment tool configured to be inserted into the shaft and to engage fixedly with said handle, said treatment tool has an active part at a distal portion of the treatment tool, such that the movement mechanism moves the shaft forwards and backwards, thereby respectively covering and revealing the active part of the treatment tool through said open distal end of the shaft.

* * * * *